United States Patent [19]

Craig et al.

[11] Patent Number: 5,004,688

[45] Date of Patent: Apr. 2, 1991

[54] PURIFICATION OF HEPATITIS PROTEINS

[75] Inventors: William S. Craig; Robert S. Siegel, both of San Diego, Calif.

[73] Assignee: Phillips Petroleum Company, Bartlesville, Okla.

[21] Appl. No.: 181,934

[22] Filed: Apr. 15, 1988

[51] Int. Cl.⁵ ..................... C12P 21/06; C12N 15/00; C07K 13/00

[52] U.S. Cl. .............................. 435/69.3; 435/235.1; 530/350

[58] Field of Search ..................... 435/69.3, 412, 235; 530/350

[56] References Cited

U.S. PATENT DOCUMENTS

| | | |
|---|---|---|
| 4,515,714 | 5/1985 | Kawahara et al. |
| 4,533,596 | 8/1985 | Lewis et al. |
| 4,612,283 | 9/1986 | Sugahara et al. |
| 4,683,293 | 7/1987 | Craig. |

FOREIGN PATENT DOCUMENTS

| | | |
|---|---|---|
| 0138167A1 | 10/1984 | European Pat. Off. |
| 0155007A2 | 3/1985 | European Pat. Off. |
| 0168234A2 | 7/1985 | European Pat. Off. |
| 0204680 | 5/1986 | European Pat. Off. |
| 0226846 | 11/1986 | European Pat. Off. |
| 0185391 | 12/1986 | European Pat. Off. |

OTHER PUBLICATIONS

Biotechnology, vol. 5, No. 5, May 1987, pp. 479–485, New York, U.S.; J. M. Cregg et al.: "High-Level Expression and Efficient Assembly of Hepatitis B Surface Antigen in the Methylotrophic Yeast, *Pichia pastoris*".

Experientia, vol. 34, pp. 414–415 (1978)–Neurath et al.

*Primary Examiner*—Robin L. Teskin
*Assistant Examiner*—Beth A. Burrous
*Attorney, Agent, or Firm*—J. E. Phillips

[57] ABSTRACT

The present invention pertains to a process for recovering hepatitis B surface antigen from recombinant *Pichia pastoris* cells comprising:
(a) lysing said yeast cells in the presence of a buffered chaotropic salt and separating the hepatitis B surface antigen-containing supernatant from said lysed cells;
(b) subjecting the heptatis B surface antigen-containing supernatant obtained in step (a) to conditions suitable to precipitate lipids and contaminant proteins from said supernatant;
(c) subjecting the hepatitis B surface antigen-containing supernatant obtained in step (b) to diafiltration;
(d) contacting the hepatitis B surface antigen-containing retentate obtained in step (c) with silica;
(e) washing contaminant proteins from the resulting silica-adsorbed hepatitis B surface antigen with a buffer having a pH within the range of 6–8;
(f) eluting the hepatitis B surface antigen from the silica with a buffered eluant having a pH within the range of 9.5–11.0 containing from 0.5 to 8 molarity of urea;
(g) subjecting the hepatitis B surface antigen-containing fraction obtained in step (f) to a gel filtration step suitable to separate said hepatitis B surface antigen from contaminant proteins; and
(h) subjecting the hepatitis B surface antigen-containing fraction obtained in step (g) to an anion exchange chromatography step suitable to separate said hepatitis B surface antigen from contaminant proteins.

8 Claims, No Drawings

PURIFICATION OF HEPATITIS PROTEINS

The present invention pertains to a process for the purification of hepatitis B surface antigens from *Pichia pastoris* yeast cells.

The hepatitis B virus induces an infection known as hepatitis B. Chronic infection with the virus can lead to hepatocirrhosis and hepatocarcinomas.

At the current time, there is not a cure for individuals infected with the hepatitis B virus. Therefore, current medical therapy centers on prophylaxis via vaccination.

The vaccine's active constituent is a polypeptide known as the hepatitis B surface antigen. This polypeptide naturally occurs on the surface of the hepatitis B virus.

One method for producing this peptide is to isolate it from the blood of individuals infected with the hepatitis B virus. However, due to the current fear of communicating diseases such as AIDS via blood products, this process has fallen from favor.

An alternative method is to produce the hepatitis B surface antigen via genetic engineering. The gene for the hepatitis B surface antigen polypeptide can be cloned into, for example, either a yeast, bacteria, or mammalian cell.

The genetically altered cell can then be grown in a manner so that the hepatitis B surface antigen polypeptide will be expressed and assembled into particles.

Although the hepatitis B surface antigen polypeptide can be successfully produced in recombinant cells, problems still exist with current methods utilized in recovery of the polypeptide from the cell and purifying it.

For example, the most commonly used purification method of hepatitis B surface antigen is a density gradient centrifugation. However, this method requires the use of a large amount of cesium chloride and sucrose, as well as the use of an ultracentrifugal machine and also various rotors in accordance with the degree of purification and scale thereof, and hence, this method is not suitable in view of high cost.

In U.S. Pat. No. 4,683,293 issued July 28, 1987, it was discovered that lipophilic proteins such as hepatitis B surface antigen produced by genetically modified strains of *Pichia pastoris* could be selectively recovered by the use of a lysis buffer containing chaotropic salts. While such a process is considered to represent a significant advance in the purification of lipophilic proteins, there still remains the need for an overall process to permit the recovery of such proteins as the hepatitis B surface antigen in a form which is suitable for use in the preparation of a vaccine.

Thus, it would be a valuable contribution to the art to develop an overall process that is amenable to being carried out on an industrial scale for the recovery of the hepatitis B surface antigen particle from yeast cells in a state of purity sufficient to be incorporated directly into a vaccine.

It is an object of the present invention to provide a process for recovering the hepatitis B surface antigen particle in a state of purity sufficient to be incorporated directly into a vaccine and in a manner that is amenable to being carried out on an industrial scale.

Other aspects and objects of the present invention will become apparent hereinafter.

In accordance with the present invention, it has been discovered that the hepatitis B surface antigen particle can be recovered and purified from a yeast cell in a process comprising:

a. lysing said yeast cell in the presence of a chaotropic salt and separating the hepatitis B surface antigen-containing supernatant from the lysed cell pellet;

b. subjecting the hepatitis B surface antigen-containing supernatant obtained in step (a) to conditions suitable to precipitate lipids and contaminating proteins from said hepatitis B surface antigen-containing supernatant and removing the precipitated residue from said hepatitis B surface antigen-containing supernatant;

c. subjecting the hepatitis B surface antigen-containing supernatant obtained in step (b) to concentration and diafiltration;

d. contacting the hepatitis B surface antigen-containing retentate obtained in step (c) with silica;

e. washing non-hepatitis B surface antigen proteins from said silica with an appropriate buffer having a pH in the range of 6 to 8;

f. eluting said hepatitis B surface antigen from the silica with an appropriate buffer having a pH in the range of 9.5 to 11.0 and containing urea present in the concentration of from 0.5 to 8 molarity;

g. subjecting the hepatitis B surface antigen-containing fraction obtained in step (f) to gel filtration with a material having a molecular weight exclusion limit suitable to separate the hepatitis B surface antigen particle from contaminants;

h. contacting the hepatitis B surface antigen-containing fraction obtained in step (g) with an anion exchange resin; and i. eluting the hepatitis B surface antigen particle from the anion exchange resin with a suitable buffer having a pH in the range of 6 to 9.

The process of the present invention is useful with any transformed yeast capable of expressing a hepatitis B surface antigen. Representative examples of suitable transformed yeasts can be selected from the group consisting of those yeasts belonging to the genera of Candida, Kloeckera, Saccharomyces, Schizosaccharomyces, Rhodotorula, Hansenula, Torulopis, Pichia and Kluyveromyces. An especially preferred yeast is *Pichia pastoris*.

Typically, yeasts are cultured by growing them on a suitable carbon energy source, under aerobic aqueous fermentation conditions employing an assimilable nitrogen source, mineral salts, molecular oxygen with suitable pH and other controls, as are known in the art. The exact manner in which the yeast is grown is not critical to the practice of the present invention.

As known to those skilled in the art, hepatitis B virus genomes are known to produce three variations of the hepatitis B surface antigen polypeptide. These variations are commonly referred to as the S-form, pre $S_1$-form and the pre $S_2$-form. The current process is amenable for recovering and purifying particles comprised of any of these forms of the polypeptide, e.g., the particles may be comprised of a mixture of hepatitis B surface antigen polypeptides.

As used in this application, the term hepatitis B surface antigen refers to particles of the S-form, pre $S_1$-form, and the pre $S_2$-form and mixtures thereof.

The first step of the present invention is to lyse the yeast cells in the presence of a chaotropic salt (U.S. Pat. No. 4,683,293). Typically the cells will be lysed by homogenization in a bead mill.

As employed in this disclosure, the term "chaotropic salt" refers to salts whose anions favor the transfer of apolar groups to water. Such salts include compounds which contain the thiocyanate anion, halide anions such as iodide and bromide, and hypohalite anions such as perchlorate, as well as cations such as, for example, lithium, calcium, and barium.

Representative examples of suitable chaotropic salts can be selected from the group consisting of sodium thiocyanate, potassium thiocyanate, sodium iodide, potassium iodide, sodium hypochloride, lithium chloride, lithium bromide, guanidinium hydrochloride, guanidinium thiocyanate, urea, and the like. Potassium thiocyanate is presently preferred.

It is presently preferred that the chaotropic salt be present in the molar concentration of about 1 up to about 8.

It is also preferred that the chaotropic salt be buffered to maintain a pH in the range of about 6 to about 8. As known to those skilled in the art, there are numerous buffer systems capable of maintaining a pH within the range of from 6-8. Any of these buffer systems that are compatible with the chosen salt are suitable for use with the present invention. The currently preferred buffer is sodium phosphate.

If desired, protease inhibitors can be present in the chaotropic salt medium. Representative examples of suitable protease inhibitors can be selected from the group consisting of phenylmethyl sulfonyl fluoride, and diisopropyl fluorophosphate.

Typically the cell lysis with the chaotropic salt will be conducted at a temperature range of from 0°-10° C., in order to further minimize proteolytic degradation.

After the yeast cells have been lysed, it is presently preferred that the hepatitis B surface antigen-containing supernatant be separated from the lysed cell pellet prior to further purification. This separation can be accomplished by centrifugation or any other conventional method.

It is presently preferred that the lysed cell pellet obtained in the extraction with the chaotropic salt be subjected to an additional washing with a buffer having a pH in the range of from 6-8 in order to remove any residual hepatitis surface antigens remaining in the cell pellet.

If desired, the buffered chaotropic salt can be used to wash the cell pellet.

After the lysed cell pellet has been washed, it is preferred that the resulting supernatant be separated from the cellular debris associated with the lysed cell pellet and combined with the supernatant obtained earlier for further purification.

The next step in the purification is to subject the hepatitis B surface antigen-containing supernatant to conditions suitable to precipitate lipids and contaminating proteins from the hepatitis B surface antigen-containing supernatant. One suitable method of causing this precipitation is to heat the supernatant to a temperature range of from 45°-55° C., preferably 47°-50° C. for a period of time ranging from 10 to 30 minutes.

Another suitable method for precipitating the lipids and contaminant proteins from the supernatant is to heat the supernatant in the presence of an acid.

Sufficient acid should be added so that the pH of the hepatitis B surface antigen-containing supernatant is lowered to a pH within the range of from about 5.0 to about 6.0.

The acid utilized in the process can be either an inorganic acid or an organic acid. Suitable acids can be selected from the group consisting of hydrochloric acid, sulfuric acid, phosphoric acid, acetic acid, oxalic acid, nitric acid, perchloric acid, or formic acid.

The acidification treatment is preferably carried out at a temperature of not higher than 30° C., more preferably not higher than 20° C., i.e., at a range of 4° C. to 30° C., more preferably 4° C. to 20° C.

After the precipitation step, it is preferred that the precipitated cellular components be separated from the hepatitis B surface antigen-containing supernatant. This can be accomplished by any conventional separation technique such as centrifugation or decantation.

If acidification is used in the precipitation step, then it is preferred that the hepatitis B surface antigen-containing supernatant be treated with sufficient base to return the pH to a range of about 6 to 8, preferably about 6.5, prior to further purification.

The particular base utilized in returning the pH to about 6–8 is not critical to the practice of the present invention. Representative examples of suitable bases can be selected from the group consisting of potassium hydroxide, sodium hydroxide and ammonium hydroxide.

The next step in the purification is to subject the hepatitis B surface antigen-containing supernatant to concentration and diafiltration. The concentration and diafiltration should be conducted with a membrane having a molecular weight exclusion limit sufficient to prevent the passage of the hepatitis B surface antigen through the membrane, but yet capable of allowing the passage of contaminant peptides and electrolytes.

Any commercially available concentration membrane having a molecular weight exclusion limit within the range of from 5000–500,000; preferably 75,000–100,000 is suitable for use in the present process.

It is also preferred that the concentration membrane be utilized to remove the chaotropic salt. This can be accomplished by adding 1 to 2 volumes of a chaotropic-free buffered solution having a pH within the range of from 6–8 to the hepatitis B surface antigen-containing supernatant after the initial concentration and repeating the concentration sequence.

Each additional equal volume of buffer will dilute the concentration of the chaotropic salt in the hepatitis B surface antigen-containing solution by a factor of about 50%. Thus, these additional volumes will gradually remove the chaotropic salt from the hepatitis B surface antigen-containing solution.

The next step in the purification scheme is to subject the hepatitis B surface antigen-containing supernatant to adsorption chromatography with silica.

The adsorption chromatography can be accomplished by a column method or by a batch method. The batch method is currently preferred. Silica suitable for use with the process of the present invention includes either particulate silica hydrate or silica anhydrate having an accessible surface area within the range of from 100 $mm^2/gm$ to 500 $mm^2/gm$. A suitable particulate silica is available under the tradename Aerosil 380 from the DeGussa Corp. of New Jersey.

In the batch method, the particulate silica is dispersed in sufficient water to produce a silica slurry containing from 40–60 wt % of silica.

The silica slurry is then contacted with the hepatitis B surface antigen-containing supernatant.

The quantity of silica slurry utilized should be such that, when the initial particle concentration is $\geqq 1\%$ of the total extractable protein from the lysed cell extract, then for every 1 mg of hepatitis B surface antigen activity present in the supernatant, 50–100 mg of silica is added to the supernatant. Preferably about 60 mg of silica is added for every 1 mg of AUSRIA activity present when the initial particle concentration is ≧1%. When the particle concentration in the lysed cell extract is <1%, then the silica quantity should be increased proportional to the decreased particle concentration.

AUSRIA II Analysis Kit is available commercially from Abbott Laboratories of Chicago, Ill.

After the hepatitis B surface antigen-containing supernatant has been contacted with the silica solution, it is preferred that the resulting mixture be stirred together for a period of time ranging from 15 minutes to 4 hours.

After the hepatitis B surface antigen-containing solution is allowed to contact the silica for an appropriate period of time, it is preferred that the supernatant be separated from the silica-bound hepatitis B surface antigens. This can be accomplished by centrifugation and decantation or any other technique conventionally used.

The next step in the purification is to remove the contaminant proteins from the silica. This can be accomplished by washing the silica with a buffered solution having a pH in the range of 6 to 8, preferably about 7.2. As is known to those skilled in the art, there are numerous buffer systems available for maintaining a pH within the range of from 6–8. Any of these buffer systems are suitable for use with the present invention. The presently preferred buffer system is a sodium phosphate-sodium chloride buffer system.

It is currently preferred that the silica be washed several times with 5 to 15 volumes of the buffer each time to insure removal of the containment proteins. One way in which to monitor the removal of contaminant proteins is to measure the absorbance of each wash at 280 nm. When the absorbance reaches the same unchanging minimum value, then the washing process is complete.

After the contaminant proteins have been removed from the silica, the hepatitis B surface antigen can be eluted from the silica by contacting the silica with a suitable buffer containing urea, present in a concentration of from 0.5 to 3 molarity.

Suitable buffers will have a pH in the range of 9.5 to 11. As is known to those skilled in the art, there are numerous buffer systems capable of maintaining a pH within the range of from 9.5–11. Any of these buffer systems are suitable for use with the present invention. Presently preferred is a sodium carbonate-sodium bicarbonate buffer.

If the batch method has been utilized, then it is preferred that 8–12 volumes of the urea-containing buffer be allowed to contact the silica for a period of time ranging from 1 to 4 hours, preferably about 2 hours. After this period of time, the supernatant containing the hepatitis B surface antigen is separated from the silica and saved for further purification.

It is currently preferred that the silica be subjected to additional elution with 8–12 volumes of the buffered urea. The additional hepatitis B surface antigen-containing fractions produced are combined with the earlier hepatitis B surface antigen-containing fraction and subjected to further purification.

If the column method is utilized then a chromatography column is packed with the particulate silica and the hepatitis B surface antigen-containing supernatant is contacted with the column. The contaminant proteins are washed from the silica with a buffer having pH in the range of 6–8 as described supra for the batch method. The hepatitis B surface antigen can be eluted with a urea buffer having a pH within the range of from 9.5–11 as described supra for the batch method.

Preferably, the hepatitis B surface antigen-containing fraction is then subjected to additional diafiltration steps in order to remove the urea. A diafiltration system should be utilized having a membrane with a molecular weight limitation such that the hepatitis B surface antigen will not pass through it.

Suitable membranes are those having a molecular weight limitation within the range of from 5,000–500,000.

The urea is removed from the hepatitis B surface antigen-containing fraction by subjecting the fraction to repeated diafiltrations during which an additional volume of a nonurea-containing buffer having a pH within the range of from 6–8 is added to the hepatitis B surface antigen-containing fraction. These repeated diafiltrations with additional buffer will gradually dilute the urea from the solution.

The next step in the purification is to subject the hepatitis B surface antigen-containing fraction to gel filtration.

It is currently preferred that the gel filtration be conducted on a chromatography column that has been packed with an agarose gel. Other suitable polar matrixes which can be utilized to pack the column can be selected from, but not limited to, the group consisting of dextran gels and polyacrylamide gels.

The polar matrix utilized as the packing material for the gel filtration should have a molecular weight exclusion limit of at least one million.

Prior to contacting the hepatitis B surface antigen-containing fraction with the chromatography column, the column should be equilibrated with an appropriate buffer to prevent the hepatitis B surface antigen from adsorbing to the packing material. Suitable buffers will have a pH in the range of 6 to 9. As known to those skilled in the art, there are numerous buffers capable of maintaining a pH range of 6–9. Any of these buffers are suitable for use with the present invention. Presently preferred is a tris(hydroxy methyl)-aminomethane(-TRIS) chloride buffer.

After the column has been equilibrated, the hepatitis B surface antigen-containing fraction should be contacted with the packing material in the column.

The buffer utilized in equilibration of the column is also utilized in washing both the contaminate proteins and the hepatitis B surface antigens through the column.

As known to those skilled in the art, those molecules having the largest molecular weight will pass through the column first, with smaller molecules following. The column should continuously be washed with an appropriate buffer until the hepatitis B surface antigens have been eluted.

The presence of hepatitis B surface antigen in the eluant can be detected by gel electrophoresis or by any of the commercially available analysis kits that are sensitive for hepatitis B surface antigen. One such suitable kit is the AUSRIA II which is available from Abbott Laboratories.

Those fractions which tested positive for possessing hepatitis B surface antigens are pooled together and optionally subjected to concentration. One suitable concentration means is ultrafiltration.

The hepatitis B surface antigen-containing fractions are then subjected to further purification by ion exchange chromatography. It is presently preferred that the purification be conducted with an anion exchange ligand. The currently preferred anion exchange ligand is a diethyl aminoethyl cation.

As known to those skilled in the art, the anion exchange ligand will be introduced into a polyacrylamide gel resin or a carbohydrate polymer resin such as cellulose or dextran and the chromatography column will be packed with this material. Column configuration can be, but is not limited to, either conventional vertical flow or radial flow. Cellulose is currently the preferred resin.

Prior to contacting the hepatitis B surface antigens with the anion exchange resin, the resins should be equilibrated with an appropriate buffer having a pH in the range of 6 to 9.

Numerous buffers are capable of maintaining this pH range. Any of these buffers are suitable for use with the present invention. Presently preferred is a TRIS-chloride buffer.

After equilibration, the hepatitis B surface antigen-containing fractions should be contacted with the anion exchange resin.

It is currently preferred that the hepatitis B surface antigens be eluted from the anion exchange resin by linear gradient elution. This can be accomplished by a linear change in ionic strength or a linear change in pH. Initially, the column is washed with a buffer system identical to that used in the equilibration step. Gradually the solvent composition is changed by introducing an electrolyte into the buffer system and gradually increasing the concentration of the electrolyte up to a molarity of about 0.3 molar.

It is currently preferred that the electrolyte be sodium chloride although other electrolytes are equally efficacious.

It is currently preferred that the various fractions obtained as the result of the gradient elution be tested for hepatitis B surface antigen content. This can be conducted in the manner in which the effluent from the gel filtration was tested.

Those fractions containing hepatitis B surface antigen are pooled together. If desired, the resulting pooled hepatitis B surface antigen-containing fractions can be concentrated by ultrafiltration.

The hepatitus B surface antigen obtained via the purification outlined above is now at least of a purity level that it can be incorporated directly into a vaccine.

The following example is presented to further illustrate the advantage of this invention. It should not be construed, however, as limiting the invention in any way.

EXAMPLE I

This Example demonstrates the utility of the present invention in purifying hepatitis B surface antigens that have been produced in transformed *Pichia pastoris* cultures.

A culture of *Pichia pastoris* (GS115, NRRL Y-15851) cells were tranformed with a vector pBSAGI5I (available in an *E. coli* host from the Northern Regional Research Center of the U.S. Department of Agriculture, Peoria, Ill., with Accession No. NRRLB-18021).

These cultures of *Pichia pastoris* were fermented by conventional techniques up to a cell density of 264 g/L wet weight.

1900 mls of the fermentation broth was separated from the fermentation vessel. This fermentation broth was centrifuged at 8500 rpm (RCF at $r_{ave}=7700$) for approximately 10 minutes and the resulting supernatant was discarded.

A chaotropic buffer was prepared for the extraction step which contained potassium thiocyanate at a concentration of 3M and sodium phosphate at a concentration of 10 mM. The protease inhibitor, phenylmethyl sulfonyl fluoride, was also added to a concentration of 1 mM. The resulting buffer had a pH of 7.5.

The lysis step was accomplished by agitating in a bead mill 500 grams of cells from the pellet in 1500 mls of the chaotropic buffer in the presence of 500 mls of 0.5 mm glass beads.

The cell-bead mixture was centrifuged for 15 minutes at 12,500 rpm (RCF at $r_{ave}=16,000$). The supernatant was separated from the cell-bead mixture by decantation and saved for subsequent purification.

The cell-bead mixture was then subjected to an additional washing with 1,000 mls of the chaotropic buffer. The resulting supernatant was then separated from the cell-bead mixture and saved for further purification.

The extraction with a chaotropic salt was conducted at a temperature of 4° C. All other purification steps were also conducted at 4° C. unless otherwise noted. This was done in order to minimize proteolytic degradation.

The supernatants were combined and subjected to precipitation by warming the supernatant to room temperature in a water bath. Once the supernatant had attained room temperature, one normal phosphoric acid was added to the supernatant in an amount to lower pH of the supernatant from 7.5 to 5. The solution was then allowed to stand at room temperature for approximately 30 minutes. During this time, contaminant proteins and lipids were precipitated from the hepatitis surface antigen-containing supernatant.

The supernatant was cooled to 4° C. and centrifuged for 15 minutes at 12,500 rpm. The supernatant was decanted in order to separate it from the precipitated debris.

The pH of the supernatant was then raised to 6.5 by adding one normal sodium hydroxide.

At this point there were 3,120 mls of hepatitis B surface antigen-containing supernatant. An AUSRIA II assay was conducted. This assay showed that there were 236 mg of hepatitis B surface antigen in the supernatant. This represented an 80.5% recovery.

The hepatitis B surface antigen-containing solution was then subjected to concentration and diafiltration on an Amicon hollow fiber ultrafiltration system having a molecular weight exclusion limit of 100,000.

After the initial concentration to approximately 0.5 liters, 1 liter of a sodium phosphate buffer having a pH of 7.5 was added to the hepatitis B surface antigen-containing supernatant and the resulting mixture was subjected to an additional concentration. This was repeated two times until the potassium thiocyanate was diluted from solution.

After the potassium thiocyanate had been removed from the hepatitis B surface antigen-containing supernatant by diafiltration, another AUSRIA II assay was conducted on the 405 mls of retentate. This assay showed that there were 231 mg of hepatitis B surface antigen, representing a 78.8% recovery.

The hepatitis B surface antigen-containing supernatant was then batch bound to silica, having an accessible surface of 380 m²/g.

This was accomplished in the following manner. First, the dry silica was prepared as a 50% slurry (dry weight/volume) with distilled water. This produced a mixture with 50 mg of silica per ml of slurry.

275 mls of the silica slurry were added to the hepatitis B surface antigen-containing supernatant and the mixture was stirred slowly at room temperature for 2 hours.

The hepatitis-silica mixture was then cooled to 4° C. and centrifuged for 15 minutes at 5,000 rpm (RCF at $r_{ave}=2500$). The resulting supernatant was discarded.

The silica was then washed with 500 mls of a phosphate buffer having a pH of 7 and containing 0.15M NaCl. The rinse was discarded. The washing steps with the phosphate buffer were continued until the absorbance at 280 nm from the supernatant reached minimum unchanging value.

The hepatitis B surface antigen was then eluted from the silica with a buffer containing 25 mM sodium carbonate, 25 mM sodium bicarbonate, and 1 molar urea. The final pH of the buffer was 10.

The hepatitis-silica mixture was placed in 500 mls of the urea buffer and stirred at room temperature for 2 hours.

The buffered urea solution, containing the silica/hepatitis was cooled to 4° C. and centrifuged for 15 minutes at 5,000 rpm. The supernatant was decanted and saved for further purification.

The silica was then eluted with a second 500 ml volume of urea, buffered in the same manner as the first. The resulting supernatant was combined with the first supernatant and subjected to a concentration and diafiltration step in order to remove the urea.

At this point, the hepatitis B surface antigen-containing supernatant was subjected to concentration on an Amicon hollow filter diafiltration system having a membrane with a molecular weight exclusion limit of 100,000.

After this initial concentration to approximately 100 mls, 200 mls of a 10 mM sodium phosphate buffer having a pH of 7.54 was added to the hepatitis B surface antigen-containing supernatant and subjected to an additional concentration. This step had the effect of diluting out the urea. This procedure was repeated 2 times which had the effect of removing 89% of the urea from the hepatitis B surface antigen-containing fraction.

After diafiltration the hepatitis B surface antigen-containing fraction was centrifuged for 15 minutes at 16,000 rpm.

An AUSRIA II assay was conducted at this point. The assay showed that there was 234 mg of hepatitis present, representing a 64.5% recovery.

The hepatitis B surface antigen-containing supernatant was then subjected to top gel filtration.

A commercially available Sepharose CL4B size exclusion column was utilized. This column had a volume of 2 liters and was packed with an argarose gel having a molecular weight exclusion limit of $20 \times 10^6$.

The hepatitis B surface antigen-containing fraction was then contacted with this column. The hepatitis was eluted from the column with 25 mm of TRIS-chloride, having a pH of 8.

The fractions were collected as they were eluted off the column and assayed for hepatitis B surface antigen content. Those fractions with hepatitis B surface antigen activity, based on polyacrylamide gel electrophoresis analysis, were pooled and saved for later purification. The assay utilized was the AUSRIA II assay test which is commercially available from Abbott labs.

The pooled fractions had a total of 170 mg of hepatitis B surface antigen activity, which represents a 63.1% recovery.

This hepatitis B surface antigen-containing fraction pool was then concentrated using an Amicon YM 30 filter.

The concentrated hepatitis B surface antigen-containing fraction was then subjected to ion exchange chromatography.

The ion exchange chromatography was conducted on a column utilizing a diethyl aminoethyl cation that had been bound to a cellulose support matrix. This column was equilibrated with a TRIS-chloride buffer having a pH of 8.

After the equilibration of the resin, the hepatitis B surface antigen-containing fraction pool was contacted with the ion exchange chromatography resin.

The hepatitis B surface antigen was then eluted from the resin by linear gradient elution, utilizing a TRIS-chloride buffer having a pH of 8 and a sodium chloride concentration varying from 0–0.3M.

The fractions were collected as they were eluted from the chromatography column and were assayed for hepatitis B surface antigens as previously described. Samples of those fractions showing hepatitis B surface antigen activity were then subjected to silver staining and the resulting gels were analyzed to confirm the presence and purity of hepatitis B surface antigen.

Those fractions possessing hepatitis B surface antigen were pooled together. A further AUSRIA II assay was conducted and showed that there were 63 mg of hepatitis B surface antigen present, representing a 42% recovery. The product as approximately 95% pure.

The hepatitis B surface antigen-containing solution was then filtered through a 0.2 micron filter and stored at $-70°$ C.

Thus, this example demonstrates that hepatitis B surface antigen proteins can be recovered from yeast cells by the present invention.

This example has been provided merely to illustrate the practice of the invention and should not be read as to limit the scope of the invention or the appended claims in any way.

Reasonable variations and modification, not departing from the essence and spirit of the invention, are contemplated to be within the scope of patent protection desired and sought.

That which is claimed is:

1. A process for recovering hepatitis B surface antigen from *Pichia pastoris* cells comprising:
    (a) lysing said yeast cells in the presence of a buffered chaotropic salt, wherein said chaotropic salt is selected from the group consisting of sodium thiocyanate, potassium thiocyanate, sodium iodide, potassium iodide, sodium hypochlorite, lithium chloride, lithium bromide, guanidiniium hydrochloride, guanidinium thiocyanate, and urea, wherein said chaotropic salt is present in the concentration of from about 1 molar to about 8 molar, and wherein said chaotropic salt is buffered by a buffer system having a pH within the range of about 6 to about 8;
    (b) subjecting the hepatitis B surface antigen-containing supernatant obtained in step (a) to conditions suitable to precipitate lipids and contaminant proteins from said supernatant wherein said precipitation of lipids and contaminant proteins is accomplished by heating said hepatitis B surface antigen-containing supernatant to a temperature range of about 45° to about 55° C. for a period of time ranging from about 10 to about 30 minutes;

(c) subjecting the hepatitis B surface antigen-containing supernatant obtained in step (b) to diafiltration wherein said diafiltration is conducted with a membrane having a molecular weight exclusion limit within the range of about 5,000 to about 500,000;

(d) contacting the hepatitis B surface antigen-containing retentate obtained in step (c) with silica wherein said silica has an accessible surface area with the range of 100 $m^2$/gm to 500 $m^2$/gm and wherein, when the initial particle concentration is $\geq 1\%$ of the total extractable protein from the lysed cell extract, then for every 1 mg of hepatitis B surface antigen activity present in said hepatitis B surface antigen-containing supernatant, there is utilized 50–100 mg of silica, and wherein, when the initial particle concentration is <1% of the total extractable protein from the lysed cell extract, then for every 1 mg of hepatitis B surface antigen activity present in said hepatitis B surface antigen-containing supernatant, there is utilized a corresponding proportional increase in silica from a base of 50–100 mg of silica per 1%;

(e) washing contaminant proteins from the resulting silica-adsorbed hepatitis B surface antigen with a buffer having a pH within the range of about 6 to about 8;

(f) eluting the hepatitis B surface antigen from the silica with a buffered eluant having a pH within the range of about 9.5 to about 11.0 containing from 0.5 to 8 molarity of urea;

(g) subjecting the hepatitis B surface antigen-containing fraction obtained in step (f) to gel filtration step suitable to separate said hepatitis B surface antigen from contaminant proteins, rein said hepatitis B surface antigen-containing fraction is subjected to gel filtration on a polar matrix selected from the group consisting of agarose gels, dextran gels, and polyacrylamide gels, and wherein said polar matrix has a molecular weight exclusion of at least 1 million and said hepatitis B surface antigen is eluted through said polar matrix with a buffer having a pH within range of about 6 to about 9; and (h) subjecting the hepatitis B surface antigen containing fraction obtained in step (g) to an anion exchange chromatography step suitable to separate said hepatitis B surface antigen from contaminant proteins wherein said ion exchange chromatography is conducted with an anion-exchange resin utilizing a diethyl aminoethyl cation and wherein said hepatitis B surface antigen is eluted from said anion exchange resin by utilizing a buffer having a pH within the range of about 6 to about 9 and an electrolyte concentration ranging from 0 molarity to 0.3 molarity.

2. The process of claim 1, wherein said yeast cells are lysed by glass beads fracture.

3. The process of claim 1, wherein said precipitation of lipids and contaminant proteins is accomplished by heating said hepatitis B surface antigen-containing solution to a temperature range of about 4 to about 30° C. and adding sufficient quantity of an acid to lower the pH of said supernatant to a range of about 4.5 to about 5.5.

4. The process of claim 3, wherein said acid is selected from the group consisting of hydrochloric acid, sulfuric acid, phosphoric acid, acetic acid, oxalic acid, nitric acid, perchloric acid and formic acid.

5. The process of claim 3, wherein after said precipitation, sufficient base is added to raise the pH of said hepatitis B surface antigen-containing supernatant to a range of about 6 to about 8.

6. The process of claim 1 wherein said silica is present as a silica slurry containing from about 40 to about 60 wt.-% of silica.

7. The process of claim 1 wherein (a) said yeast cells are lysed in the presence of a phosphate buffer having a pH of about 7.5 and a potassium thiocyanate concentration of about 3 molar;

(b) said precipitation is conducted at a temperature of about 20° C. in the presence of phosphoric acid having a concentration sufficient to lower the pH to 5.0;

(c) after said precipitation, sufficient sodium hydroxide is added to raise the pH of said hepatitis B surface antigen-containing solution to about 6.5;

(d) said hepatitis B surface antigen-containing supernatant is diafiltered on a membrane having a molecular weight exclusion limit of 100,000 and in the presence of a phosphate buffer having a pH of about 7.5;

(e) said hepatitis B surface antigen-containing supernatant is contacted with a sufficient quantity of an about 50 wt-% silica slurry so that for every 1 mg of hepatitis B surface antigen activity present in said supernatant there is utilized 60 mg of silica;

(f) said contaminant proteins are washed from said silica with a phosphate buffered saline buffer system having a pH of about 7 and containing 0.5M NaCl;

(g) said hepatitis B surface antigen is eluted from said silica with a carbonate-bicarbonate buffer having a pH of about 10.1 and a urea concentration of about 1 molar;

(h) said hepatitis B surface antigen-containing fraction obtained in step (g) is subjected to diafiltration on a membrane having a molecular weight exclusion limit of 100,000 in the presence of a TRIS-chloride buffer having a pH of about 8;

(i) said gel filtration is conducted on an garose gel having a molecular weight exclusion of $20 \times 10^6$ and said hepatitis B surface antigen is eluted through said agarose gel with a TRIS-chloride buffer having a pH of about 8;

(j) said ion exchange chromatography is conducted with a diethyl aminoethyl cation and said hepatitis B surface antigen is eluted from said cation with TRIS-chloride buffer having a sodium chloride concentration ranging from 0–0.3 molar.

8. A process according to claim 1 wherein said yeast cells are of *Pichia pastoris* GS115 (NRRL Y-15851) transformed with pBSAGI5I (NRRLB-18021).

* * * * *